(12) United States Patent
Gerke et al.

(10) Patent No.: US 9,284,261 B2
(45) Date of Patent: *Mar. 15, 2016

(54) PHOTOLABILE PRO-FRAGRANCES

(71) Applicant: Henkel AG & Co. KGaA, Duesseldorf (DE)

(72) Inventors: Thomas Gerke, Duesseldorf (DE); Christian Kropf, Hilden (DE); Ursula Huchel, Cologne (DE); Axel Griesbeck, Cologne (DE); Agnieszka Landes, Bergheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/570,053

(22) Filed: Dec. 15, 2014

(65) Prior Publication Data

US 2015/0099810 A1 Apr. 9, 2015

Related U.S. Application Data

(63) Continuation of application No. PCT/EP2013/058683, filed on Apr. 26, 2013.

(30) Foreign Application Priority Data

Jun. 22, 2012 (DE) .......... 10 2012 210 566

(51) Int. Cl.
| | |
|---|---|
| C07C 217/74 | (2006.01) |
| C07D 207/06 | (2006.01) |
| C07C 217/22 | (2006.01) |
| C11D 3/50 | (2006.01) |
| A61K 8/41 | (2006.01) |
| A61Q 13/00 | (2006.01) |
| A61K 8/49 | (2006.01) |

(52) U.S. Cl.
CPC .............. *C07C 217/74* (2013.01); *A61K 8/416* (2013.01); *A61K 8/4913* (2013.01); *A61Q 13/00* (2013.01); *C07C 217/22* (2013.01); *C07D 207/06* (2013.01); *C11D 3/50* (2013.01); *C11D 3/507* (2013.01)

(58) Field of Classification Search
USPC .......................................... 514/102; 568/327
IPC ...................................................... C07C 217/74
See application file for complete search history.

(56) References Cited

U.S. PATENT DOCUMENTS

| | | | |
|---|---|---|---|
| 6,949,680 B2 * | 9/2005 | Herrmann | |
| 8,466,294 B2 | 6/2013 | Huchel et al. | |
| 8,604,250 B2 | 12/2013 | Gerke et al. | |

OTHER PUBLICATIONS

PCT International Search Report (PCT/EP2013/058683) dated Aug. 26, 2013.

Richert et al., "Reaction of sebacic acid with phenols and naphthols in the presence of pure boron fluoride", Bulletin de la Societe Chimique de France, Societe Francaise de Chimie, Paris, France, Nr. 7, Jan. 1, 1966, pp. 2186-2190, XP008163925, ISSN: 0037-8968.

* cited by examiner

*Primary Examiner* — Shirley V Gembeh
(74) *Attorney, Agent, or Firm* — P. Scott Smith

(57) ABSTRACT

Fragrances that provide a scent of freshness tend to be volatile and are therefore not very economical when used in typical applications such as washing or cleaning processes, so they have to be used in relatively large quantities to be able to produce adequate effects. The disclosed photolabile pro-fragrances provide a much longer-lasting sense of fragrance, in particular with a scent of freshness, when used in typical applications, thus allowing said fragrances to be used economically.

7 Claims, No Drawings

PHOTOLABILE PRO-FRAGRANCES

FIELD OF THE INVENTION

The present invention generally relates to special, cationically charged compounds which act as photolabile pro-fragrances. Furthermore, the present invention relates to washing or cleaning agents, cosmetic agents and room scenting agents that contain these compounds. Furthermore, it relates to a method for the long-lasting scenting of surfaces and likewise to a method for long-lasting room scenting.

BACKGROUND OF THE INVENTION

Washing or cleaning agents and cosmetic agents usually contain scents, which impart a pleasant odor to the agents. At the same time, the scents usually mask the odor of other ingredients so that a pleasant odor impression is obtained by the consumer.

In the sector of washing agents in particular, scents are important constituents of the composition, since the laundry should have a pleasant and also a fresh scent, both in the wet and in the dry state. With the use of scents, one is faced with the fundamental problem that these are more or less volatile compounds, but yet a long-lasting scent effect is desired. In particular in the case of those scents that represent the fresh and light notes of the perfume and, as a result of their high vapor pressure, evaporate particularly rapidly, the desired long life of the scent impression is extremely difficult to achieve.

A delayed release of scent can take place e.g. by a carrier-bound use of scents. A carrier-bound precursor of a scent is also referred to as a "pro-fragrance" or scent storage substance. In connection with this, the international patent application WO 2007/087977 discloses the use of 1-aza-3,7-dioxabicyclo[3.3.0]octane compounds as pro-fragrances for the delayed release of scent aldehydes and scent ketones by hydrolysis. An alternative possibility for delayed release of scents involves the use of so-called photoactivatable substances as pro-fragrances. The action of sunlight or of another electromagnetic radiation source of a specific wavelength induces breakage of a covalent bond in the pro-fragrance molecule, thereby releasing a scent.

WO 2011/101180 discloses the use of specific ketones as photo-activatable substances that release an active substance in the presence of light in a photochemical fragmentation. The said active substance possesses e.g. a scent-imparting activity, which is at first delayed by the photochemically induced breakdown, and released over a longer period of time on a specific surface.

The object of the present invention is to provide photoactivatable substances as pro-fragrances, which permit the delayed release of scent ketones and scent esters and which attach particularly well to surfaces, in particular to textile surfaces.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A compound of the general formula (I),

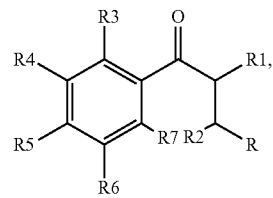

Formula (I)

wherein R denotes a substituted hydrocarbon residue with 2 to 20 C atoms, having at least one carbonyl group or ester group; R1, R2 each, independently of one another, denote hydrogen, a linear or branched, substituted or unsubstituted alkoxy group with 1 to 15 C atoms, a linear or branched, substituted or unsubstituted alkyl group or alkenyl group with 1 to 15 C atoms or a substituted or unsubstituted aryl residue; R3, R4, R5, R6 and R7 each, independently of one another, denote hydrogen, an amino group, $-NO_2$, a linear or branched, substituted or unsubstituted alkoxy group with 1 to 15 C atoms, a linear or branched, substituted or unsubstituted alkyl group with 1 to 15 C atoms, a cycloalkyl residue, acyl residue, aryl residue, $-OH$, $-NH_2$, halogen, NH-alkyl or $-N(alkyl)2$; and wherein at least one of the residues R3, R4, R5, R6, R7 denotes a quaternary ammonium residue of formula (II),

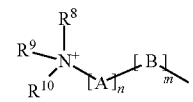

(II)

wherein A denotes a $CH_2$ or a $CH_2CH_2O$ group with n=1 to 20 and B denotes oxygen with m=0 or 1, wherein m=0 if A is a $CH_2CH_2O$ group and R8, R9, R10 each, independently of one another, denote H or a substituted or unsubstituted, alkyl, cycloalkyl, alkenyl, aryl or acyl group-containing residue, and wherein two of the residues R8, R9, R10 can in each case be joined together by ring closure.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The object of the present invention was achieved by a compound of the general formula (I),

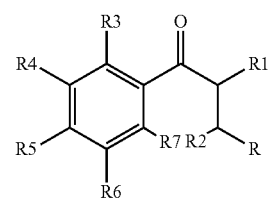

Formula (I)

wherein
R denotes a substituted hydrocarbon residue with 2 to 20 C atoms, having at least one carbonyl group or ester group, R1, R2 each, independently of one another, denote hydrogen, a linear or branched, substituted or unsubstituted alkoxy group with 1 to 15 C atoms, a linear or branched, substituted or unsubstituted alkyl group or alkenyl group with 1 to 15 C atoms or a substituted or unsubstituted aryl residue, R3, R4, R5, R6 and R7 each, independently of one another, denote hydrogen, an amino group, —NO₂, a linear or branched, substituted or unsubstituted alkoxy group with 1 to 15 C atoms, a linear or branched, substituted or unsubstituted alkyl group with 1 to 15 C atoms, a cycloalkyl residue, acyl residue, aryl residue, —OH, —NH₂, halogen, NH-alkyl or —N(alkyl)₂, and wherein at least one of the residues R3, R4, R5, R6, R7 denotes a quaternary ammonium residue of formula (II),

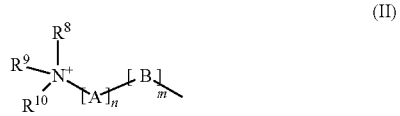

wherein A denotes a CH₂ or a CH₂CH₂O group with n=1 to 20 and B denotes oxygen with m=0 or 1, wherein m=0 if A is a CH₂CH₂O group, and R8, R9, R10 each, independently of one another, denote H or a substituted or unsubstituted, alkyl, cycloalkyl, alkenyl, aryl or acyl group-containing residue and wherein two of the residues R8, R9, R10 can in each case be joined together by ring closure.

Surprisingly, it has been found that the compounds according to the invention are particularly effective pro-fragrances, which attach particularly well to surfaces, in particular to textile surfaces. In particular the use of quaternary ammonium residues of formula (II) in compounds of formula (I) has the effect that the compounds according to the invention are particularly effective pro-fragrances, and attach particularly well to surfaces, in particular to textile surfaces. The compounds according to the invention make possible the delayed release of scent ketones, in particular of damascone, or of scent esters, in particular of cinnamic acid esters and derivatives of cinnamic acid esters. The use of the compounds according to the invention in washing, cleaning or care agents led to an improved long-term scent effect when they were used, in particular in connection with textile treatment. For example, when compounds according to the invention were used in a laundry treatment agent, such as e.g. washing agents and fabric softeners, an improved long-term scent effect of the treated laundry was found. Furthermore, corresponding products exhibit particularly good storage stability. The agents according to the invention also make it possible to reduce the total quantity of perfume that is contained in the agent, and yet to achieve odor advantages on the washed textiles, in particular with regard to the perception of freshness.

The compound according to general formula (I) is suitable as a pro-fragrance for all conventional scent ketones and scent esters which, in their free form as a scent, comprise an alpha, beta-unsaturated carbonyl unit or mesomeric forms thereof.

Preferred scent ketones are selected in particular from Buccoxime, iso-jasmone, methyl beta-naphthyl ketone, musk indanone, tonalide/Musk Plus, alpha-damascone, beta-damascone, delta-damascone, gamma-damascone, damascenone, damarose, methyl dihydrojasmonate, menthone, carvone, camphor, fenchone, alpha-ionone, beta-ionone, so-called gamma-methyl ionone, fleuramone, dihydrojasmone, cis-jasmone, iso-E-Super®, methyl cedrenyl ketone or methyl cedrylone, acetophenone, methylacetophenone, para-methoxyacetophenone, methyl beta-naphthyl ketone, benzylacetone, benzophenone, para-hydroxyphenylbutanone, celery ketone or livescone, 6-isopropyldecahydro-2-naphthone, dimethyl octenone, frescomenthe, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)indanone, 4-damascol, dulcinyl or cassione, gelsone, hexylone, isocyclemone E, methyl cyclocitrone, methyl lavender ketone, orivone, para-tertiary butyl cyclohexanone, verdone, delphone, muscone, neobutenone, plicatone, veloutone, 2,4,4,7-tetramethyloct-6-en-3-one, tetrameran or mixtures thereof. The ketones can preferably be selected from the damascones, carvone, gamma-methyl ionone, iso-E-Super, 2,4,4,7-tetramethyloct-6-en-3-one, benzylacetone, damascenone, methyl dihydrojasmonate, methyl cedrylone, Hedione and mixtures thereof. Most preferred are all the damascones and damascenone. The stored ketones can be released by the action of light comprising the wavelengths of 200 to 400 nm.

Preferred scent esters are selected from cinnamic acid esters and derivatives of cinnamic acid esters. Particularly preferred are linaloyl cinnamate, 3-phenylpropyl cinnamate, eugenol cinnamate, allyl cinnamate, benzyl cinnamate, butyl cinnamate, ethyl cinnamate, methyl cinnamate, menthyl cinnamate, heptyl cinnamate, cyclohexyl cinnamate, isoamyl cinnamate, isobutyl cinnamate, isopentyl cinnamate, isopropyl cinnamate, isoheptyl cinnamate, tetrahydrofurfuryl cinnamate and cinnamyl cinnamate. The stored esters can be released by the action of light comprising the wavelengths of 200 to 500 nm.

According to a preferred embodiment of the invention, the substituent R2 in formula (I) denotes a linear or branched, substituted or unsubstituted alkyl group with 1 to 6 C atoms, preferably 1 to 3 C atoms, and is in particular a methyl residue.

According to a preferred embodiment of the invention, in the quaternary ammonium residue of formula (II), n=1 to 6, in particular 1 to 3. It is further preferred if A denotes a CH₂ group, in particular a CH₂ group with n=1, 2 or 3.

It is particularly preferred if m=1. In particular, it is preferred if A denotes a CH₂ group with n=1, 2 or 3 and m=1.

Furthermore, a compound according to the invention of general formula (I) is preferred in which four of the five aryl substituents R3, R4, R5, R6 and R7 denote hydrogen.

It is additionally preferred that at least one of the substituents R4 and R5 each denotes a quaternary ammonium residue of formula (II). A substitution in para-position (R5) is particularly preferred since the electronic structure of the aromatic ring can be modified most effectively here, as a result of which the absorption maximum of compounds of general formula (I) can readily be adapted to a specific wavelength.

In a preferred embodiment, the substituents R3, R4, R6 and R7 therefore each denote hydrogen and the residue R5 denotes a quaternary ammonium residue of formula (II),

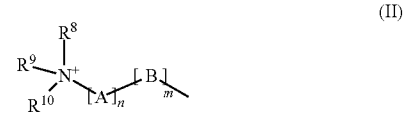

wherein A denotes a CH₂ or a CH₂CH₂O group with n=1 to 20 and B denotes oxygen with m=0 or 1, wherein m=0 if A is a CH₂CH₂O group, and R8, R9, R10 each, independently of one another, denote H or a substituted or unsubstituted alkyl, cycloalkyl, alkenyl, aryl or acyl group-containing residue and wherein two of the residues R8, R9, R10 can in each case be joined together by ring closure.

It is preferred if at least one of the residues R8, R9 and R10 denotes a methyl group. If only one of the residues R8, R9 or R10 denotes a methyl group, then it is particularly preferred if the other two residues are joined together by ring closure. If two of the residues R8, R9 and R10 denote a methyl group, then it is particularly preferred if the third residue denotes an alkyl chain with 12 to 20 carbon atoms.

According to a particularly preferred embodiment of the invention, compounds of formula (I) correspond to the following formulae (III), (IV), (V), (VI), (VII), (VIII), (IX) and (X):

(III)
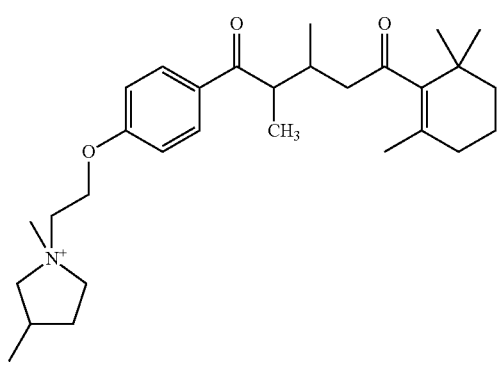

(IV)
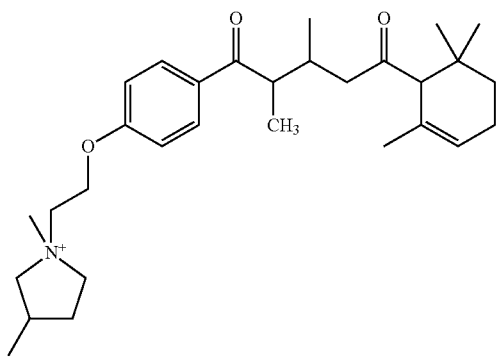

(V)
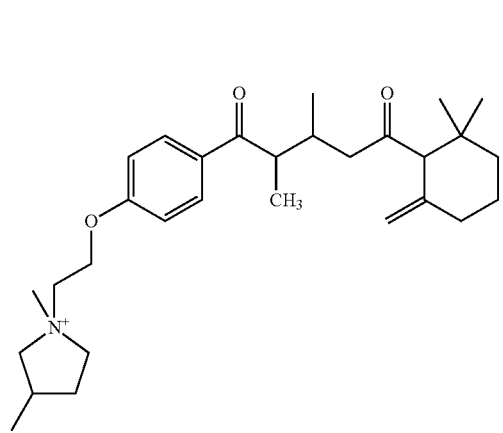

(VI)
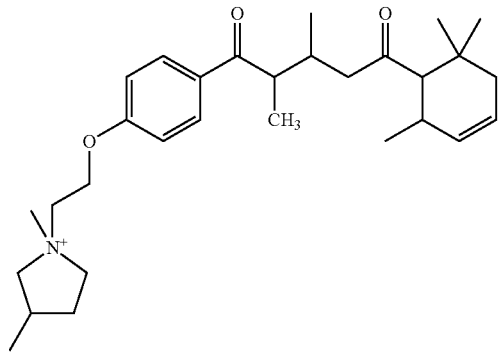

(VII)
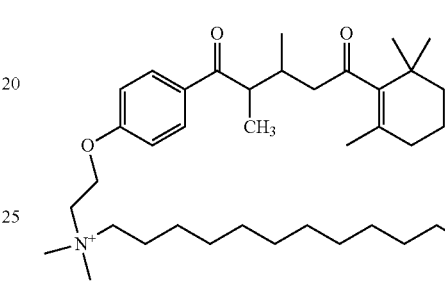

(VIII)
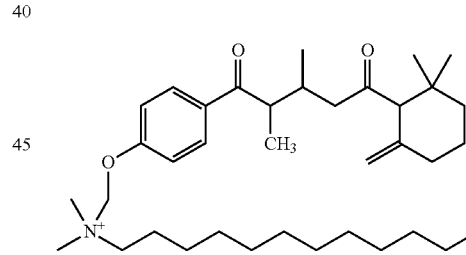

(IX)
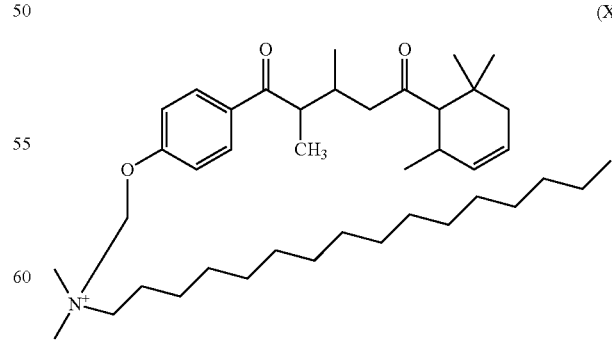

(X)

According to another particularly preferred embodiment of the invention, compounds of formula (I) correspond to the following formulae (XI), (XII), (XIII) and (XIV):

(XI)

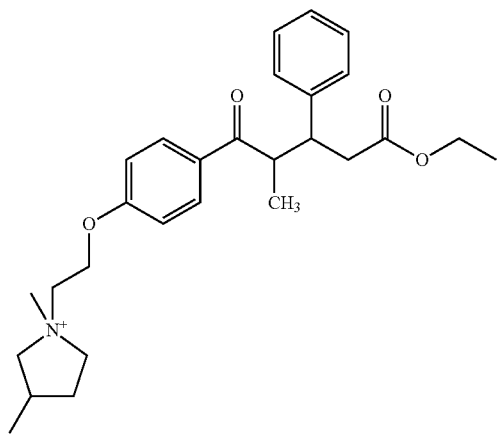

(XII)

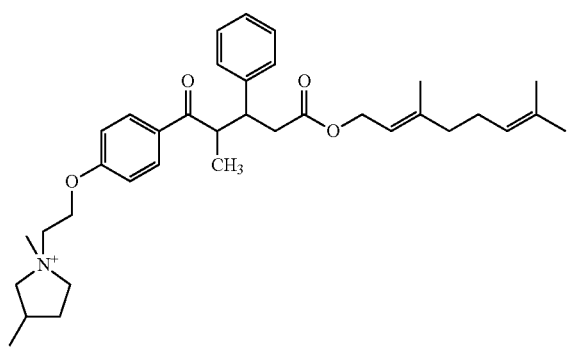

(XIII)

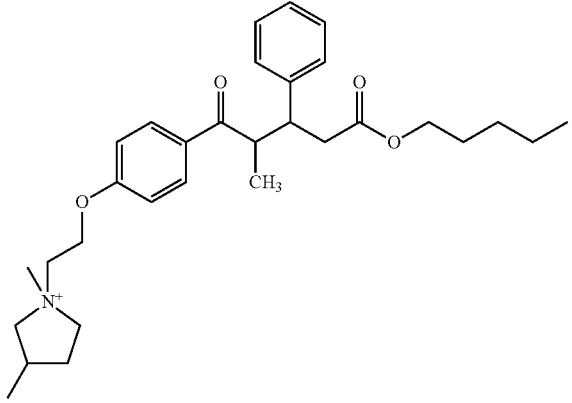

(XIV)

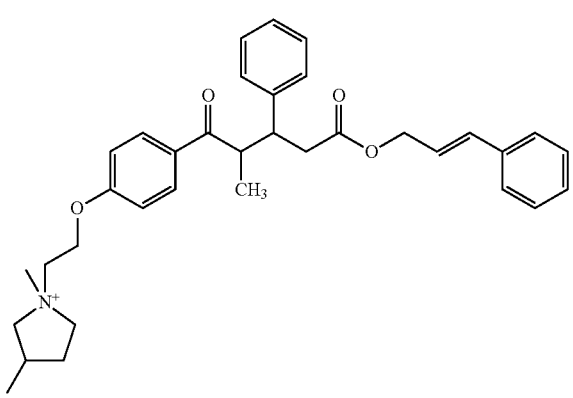

The compounds according to the invention, in particular the compounds of formulae (III) to (XIV), can be incorporated in a stable manner into the conventional washing or cleaning agent matrices, into cosmetics and existing scent compositions. Compounds of formulae (III) to (X) make possible a delayed release of the stored scent ketones, such as e.g. of damascones in the alpha, beta, gamma or delta form and of damascenones, in particular beta-damascenones. Compounds of formulae (XI) to (XIV) make possible a delayed release of the stored scent esters.

These ketones and esters impart a particularly long-lasting impression of freshness to conventional washing or cleaning agents and cosmetics. In particular the dried, washed textile benefits from the good long-term effect of a fresh scent.

The slow release of the stored scent takes place after exposure to light (electromagnetic radiation) comprising the wavelengths of 200 to 400 nm, as illustrated in simplified form in the following reaction equations:

1. Example of Release of a Scent Ketone

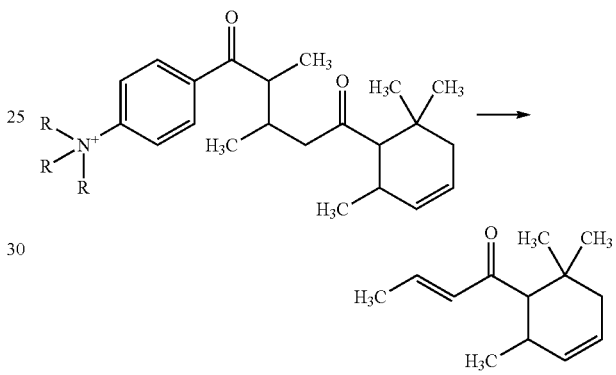

with R according to $R_8$, $R_9$, $R_{10}$ from formula (II).

2. Example of Release of a Scent Ester

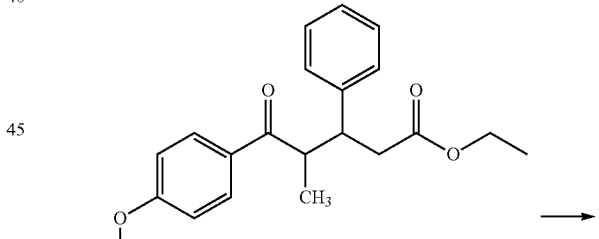

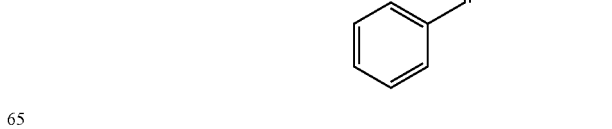

The present invention also provides a washing or cleaning agent, preferably a washing agent, fabric softener or washing auxiliary, containing at least one compound according to one of formulae (I) and/or (III) to (XIV), wherein the said compound is contained preferably in quantities of between 0.0001 and 5 wt. %, advantageously between 0.001 and 4 wt. %, more advantageously between 0.01 and 3 wt. %, in particular between 0.1 and 2 wt. %, based in each case on the total agent. Suitable cleaning agents are e.g. cleaning agents for hard surfaces, such as preferably dishwashing agents. They can also be cleaning agents such as e.g. household cleaners, all-purpose cleaners, window cleaners, floor cleaners etc. They can preferably be a product for cleaning toilet bowls and urinals, advantageously a flush cleaner for hanging in the toilet bowl, in particular a so-called toilet flusher.

According to a preferred embodiment of the invention, the washing or cleaning agent according to the invention contains at least one surfactant, selected from anionic, cationic, non-ionic, zwitterionic, amphoteric surfactants or mixtures thereof.

According to another preferred embodiment of the invention, the agent according to the invention is present in solid or liquid form.

The invention also provides a cosmetic agent containing at least one compound according to one of formulae (I) and/or (III) to (XIV), which contains the said compound preferably in quantities of between 0.0001 and 5 wt. %, advantageously between 0.001 and 4 wt. %, more advantageously between 0.01 and 3 wt. %, in particular between 0.1 and 2 wt. %, based in each case on the total agent.

The invention also provides a room scenting agent (e.g. room air freshener, room deodorant, room spray etc.), containing at least one compound according to one of formulae (I) and/or (III) to (XIV), wherein the said compound is contained preferably in quantities of between 0.0001 and 50 wt. %, advantageously between 0.001 and 5 wt. %, more advantageously between 0.1 and 3 wt. %, in particular between 0.1 and 2 wt. %, based in each case on the total agent.

According to another preferred embodiment of the invention, additional scents, in particular selected from the group comprising scents of natural or synthetic origin, preferably more volatile scents, higher boiling-point scents, solid scents and/or adherent scents, are contained in an agent according to the invention (i.e. washing or cleaning agent, cosmetic agent or room scenting agent).

Adherent scents that can be used with advantage within the framework of the present invention are, for example, essential oils, such as angelica oil, anise oil, arnica flower oil, basil oil, bay oil, bergamot oil, champaca flower oil, silver fir oil, silver fir cone oil, elemi oil, eucalyptus oil, fennel oil, fir needle oil, galbanum oil, geranium oil, gingergrass oil, guaiacwood oil, balsam gurjun oil, helichrysum oil, ho oil, ginger oil, iris oil, cajeput oil, calamus oil, chamomile oil, camphor oil, cananga oil, cardamom oil, cassia oil, pine needle oil, balsam copaiva oil, coriander oil, curled peppermint oil, caraway oil, cumin oil, lavender oil, lemon grass oil, lime oil, mandarin oil, melissa oil, ambrette seed oil, myrrh oil, clove oil, neroli oil, niaouli oil, olibanum oil, orange oil, oregano oil, palmarosa oil, patchouli oil, Peru balsam oil, petitgrain oil, pepper oil, peppermint oil, pimento oil, pine oil, rose oil, rosemary oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil, and cypress oil.

However, higher boiling-point or solid scents of natural or synthetic origin can also be employed within the framework of the present invention as adherent scents or scent mixtures, i.e. scents. These compounds include the compounds mentioned below as well as mixtures thereof: ambrettolide, alpha-amylcinnamaldehyde, anethole, anisaldehyde, anisyl alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl-n-amyl ketone, methylanthranilic acid methyl ester, p-methylacetophenone, methyl chavicol, p-methylquinoline, methyl beta-naphthyl ketone, methyl-n-nonyl acetaldehyde, methyl n-nonyl ketone, muscone, beta-naphthol ethyl ether, beta-naphthol methyl ether, nerol, nitrobenzene, n-nonyl aldehyde, nonyl alcohol, n-octyl aldehyde, p-oxyacetophenone, pentadecanolide, beta-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, gamma-undelactone, vanillin, veratrum aldehyde, cinnamaldehyde, cinnamyl alcohol, cinnamic acid, cinnamic acid ethyl ester, cinnamic acid benzyl ester. Included among the more volatile scents are, in particular, the lower boiling-point scents of natural or synthetic origin, which can be used alone or in mixtures. Examples of more volatile scents are alkyl isothiocyanates (alkyl mustard oils), butanedione, limonene, linalool, linalyl acetate and propionate, menthol, menthone, methyl n-heptenone, phellandrene, phenylacetaldehyde, terpinyl acetate, citral, citronellal.

According to a further preferred embodiment, the agent according to the invention (i.e. washing or cleaning agent, cosmetic agent or room scenting agent) has at least one, preferably more than one, active component, in particular components having washing, care-providing or cleaning activity and/or cosmetic components, which are advantageously selected from the group comprising anionic surfactants, cationic surfactants, amphoteric surfactants, nonionic surfactants, alkalizing agents, anti-wrinkle agents, antibacterial substances, antioxidants, antiredeposition agents, antistatic agents, builder substances, bleaching agents, bleach activators, bleach stabilizers, bleach catalysts, ironing aids, co-builders, scents, shrinkage preventers, electrolytes, enzymes, color protectants, coloring agents, dyes, dye transfer inhibitors, fungicides, germicides, odor-complexing substances, adjuvants, hydrotropes, rinse aids, complexing agents, preservatives, corrosion inhibitors, water-miscible organic solvents, optical brighteners, perfume carriers, pearl luster pigments, pH adjusting agents, proofing and impregnating agents, polymers, swelling and anti-slip agents, foam inhibitors, sheet silicates, soil-repelling substances, silver protectants, silicone oils, soil-release active substances, UV-protection substances, viscosity regulators, thickening agents, vitamins and/or fabric-softening compounds. Within the meaning of this invention, data for the agent according to the invention in wt. % refer, unless otherwise indicated, to the total weight of the agent according to the invention.

The quantities of the individual ingredients in the agents according to the invention, i.e. washing or cleaning agent, cosmetic agent or room scenting agent, are guided in each case by the intended use of the respective agents and the person skilled in the art is, in principle, familiar with the orders of magnitude of the quantities of the ingredients to be employed or can take them from the relevant technical literature. Depending on the intended use of the agents according to the invention, e.g. a higher or lower surfactant content will be selected. For example, the surfactant content of e.g. washing agents can usually be between 10 and 50 wt. %, preferably between 12.5 and 30 wt. % and in particular between 15 and 25 wt. %, while e.g. cleaning agents for automatic dishwashing can contain e.g. between 0.1 and 10 wt. %, preferably between 0.5 and 7.5 wt. % and in particular between 1 and 5 wt. % surfactants.

The agents according to the invention (i.e. washing or cleaning agent, cosmetic agent or room scenting agent) can contain surfactants, in which case preferably anionic surfactants, nonionic surfactants and mixtures thereof, but also cationic surfactants, are suitable. Suitable nonionic surfactants are in particular ethoxylation and/or propoxylation products of alkyl glycosides and/or linear or branched alcohols having in each case 12 to 18 C atoms in the alkyl portion and 3 to 20, preferably 4 to 10 alkyl ether groups. Furthermore, it is possible to use corresponding ethoxylation and/or propoxylation products of N-alkylamines, vicinal diols, fatty acid esters and fatty acid amides, which correspond to the above-mentioned long-chain alcohol derivatives with regard to the alkyl portion, and of alkylphenols having 5 to 12 C atoms in the alkyl residue.

Suitable anionic surfactants are in particular soaps, and those that contain sulfate or sulfonate groups with preferably alkali ions as cations. Soaps that can be used are preferably the alkali salts of saturated or unsaturated fatty acids having 12 to 18 C atoms. These fatty acids can also be employed in incompletely neutralized form. Included among the usable surfactants of the sulfate type are the salts of the sulfuric acid semiesters of fatty alcohols having 12 to 18 C atoms, and the sulfation products of the aforesaid nonionic surfactants having a low degree of ethoxylation. Included among the usable surfactants of the sulfonate type are linear alkylbenzenesulfonates having 9 to 14 C atoms in the alkyl portion, alkanesulfonates having 12 to 18 C atoms, and olefin sulfonates having 12 to 18 C atoms that are produced upon reaction of corresponding monoolefins with sulfur trioxide, as well as alpha-sulfo fatty acid esters that are produced upon sulfonation of fatty acid methyl or ethyl esters.

Cationic surfactants are preferably selected from among the esterquats and/or the quaternary ammonium compounds (QACs) in accordance with the general formula $(R^{I})(R^{II})(R^{III})(R^{IV})N^{+} X^{-}$, in which $R^{I}$ to $R^{IV}$ denote identical or different $C_{1-22}$ alkyl residues, $C_{7-28}$ aralkyl residues or heterocyclic residues, such that two or, in the case of an aromatic bond such as in pyridine, even three residues, together with the nitrogen atom, form the heterocycle, e.g. a pyridinium or imidazolinium compound, and X denotes halide ions, sulfate ions, hydroxide ions or similar anions. QACs can be produced by the reaction of tertiary amines with alkylating agents, such as e.g. methyl chloride, benzyl chloride, dimethyl sulfate, dodecyl bromide, but also ethylene oxide. The alkylation of tertiary amines having a long alkyl residue and two methyl groups can be achieved particularly easily, and the quaternization of tertiary amines having two long residues and one methyl group can also be carried out using methyl chloride under mild conditions. Amines that possess three long alkyl residues or hydroxy-substituted alkyl residues have low reactivity, and are quaternized e.g. using dimethyl sulfate. Suitable QACs are, for example, benzalkonium chloride (N-alkyl-N,N-dimethyl benzyl ammonium chloride), Benzalkon B (m,p-dichlorobenzyl dimethyl $C_{12}$-alkyl ammonium chloride), benzoxonium chloride (benzyl-dodecyl-bis(2-hydroxyethyl)ammonium chloride), cetrimonium bromide (N-hexadecyl-N,N-trimethylammonium bromide), benzethonium chloride (N,N-dimethyl-N-[2-[2-[p-(1,1,3,3-tetramethylbutyl)phenoxy]ethoxy]ethyl]benzyl ammonium chloride), dialkyldimethylammonium chlorides, such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having $C_8$ to $C_{22}$ alkyl residues, in particular $C_{12}$ to $C_{14}$ alkylbenzyldimethylammonium chloride.

Preferred esterquats are methyl-N-(2-hydroxyethyl)-N,N-di(tallow-acyl-oxyethyl)ammonium methosulfate, bis(palmitoyl)ethyl hydroxyethyl methylammonium methosulfate or methyl-N,N-bis(acyloxyethyl)-N-(2-hydroxyethyl) ammonium methosulfate. Commercially available examples are the methyl hydroxyalkyl dialkoyloxyalkylammonium methosulfates marketed by Stepan with the trademark Stepantex® or the products from BASF SE known by the trade name Dehyquart® or the products from the manufacturer Evonik Industries AG known by the name Rewoquat®.

Surfactants are contained in the agents according to the invention (i.e. washing or cleaning agent, cosmetic agent or room scenting agent) in quantitative proportions of preferably 5 wt. % to 50 wt. %, in particular of 8 wt. % to 30 wt. %. In laundry post-treatment agents in particular, preferably up to 30 wt. %, in particular 5 wt. % to 15 wt. % surfactants, among these preferably at least a proportion of cationic surfactants, are employed.

An agent according to the invention, in particular a washing or cleaning agent, preferably contains at least one water-soluble and/or water-insoluble, organic and/or inorganic builder. The water-soluble organic builder substances include polycarboxylic acids, in particular citric acid and sugar acids, monomeric and polymeric aminopolycarboxylic acids, in particular methylglycinediacetic acid, nitrilotriacetic acid and ethylenediaminetetraacetic acid as well as polyaspartic acid, polyphosphonic acids, in particular aminotris(methylenephosphonic acid), ethylenediaminetetrakis(methylenephosphonic acid) and 1-hydroxyethane-1,1-diphosphonic acid, polymeric hydroxy compounds, such as dextrin, and polymeric (poly)carboxylic acids, polymeric acrylic acids, methacrylic acids, maleic acids and copolymers of these, which can also contain small proportions of polymerizable substances without carboxylic acid functionality polymerized into them. Suitable, although less preferred, compounds from this class are copolymers of acrylic acid or methacrylic acid with vinyl ethers, such as vinyl methyl ethers, vinyl esters, ethylene, propylene and styrene, in which the proportion of acid is at least 50 wt. %. All of the aforementioned acids are generally employed in the form of their water-soluble salts, in particular their alkali salts.

Organic builder substances can, if desired, be contained in quantities of up to 40 wt. %, in particular up to 25 wt. % and preferably of 1 wt. % to 8 wt. %. Quantities close to the above upper limit are preferably employed in paste-like or liquid, in particular aqueous, agents according to the invention. Laundry post-treatment agents, such as e.g. fabric softeners, can optionally also be free from organic builder.

Suitable as water-soluble inorganic builder materials are, in particular, alkali silicates and polyphosphates, preferably sodium triphosphate, e.g. zeolite A, P or X.

Inorganic builder substances are contained in the agents according to the invention, if desired, preferably in quantities of up to 60 wt. %, in particular of 5 wt. % to 40 wt. %. Laundry post-treatment agents according to the invention, such as e.g. fabric softeners, are preferably free from inorganic builder.

Peroxygen compounds that are suitable are, in particular, organic peroxy acids or peroxy acid salts of organic acids, such as phthalimidoperoxycaproic acid, peroxybenzoic acid, or salts of diperoxydodecanedioic acid, hydrogen peroxide and inorganic salts that release hydrogen peroxide under application conditions, such as perborate, percarbonate and/or persilicate. The addition of small quantities of known bleaching-agent stabilizers, such as e.g. phosphonates, borates or metaborates, and metasilicates, as well as magnesium salts such as magnesium sulfate, may be useful.

Suitable enzymes usable in the agents are those from the class of the proteases, cutinases, amylases, pullulanases, hemicellulases, cellulases, lipases, oxidases, and peroxidases, as well as mixtures thereof. Enzymatic active substances obtained from fungi or bacteria, such as *Bacillus subtilis, Bacillus licheniformis, Streptomyces griseus, Humicola lanuginosa, Humicola insolens, Pseudomonas pseudoalcaligenes*, or *Pseudomonas cepacia*, are particularly suitable. The enzymes that are optionally used can be adsorbed onto carrier substances and/or embedded in encapsulating substances in order to protect them from premature inactivation. They are contained in the agents according to the present invention, if desired, preferably in quantities no greater than 5 wt %, in particular from 0.2 wt % to 2 wt %.

The production of the compounds according to the invention is described in the examples section with reference to the production of a pro-fragrance containing delta-damascone by way of example. The other compounds of general formula (I) and in particular all compounds of formulae (III) to (XIV) can also be obtained by the principle of this synthesis route.

According to a preferred embodiment, the teaching according to the invention can be employed to reduce the proportion of perfume in washing or cleaning agents and cosmetic agents significantly. As a result, it is possible to offer perfumed products even for those particularly sensitive consumers who, because of specific incompatibilities and irritations, can use normally perfumed products only to a limited extent or not at all.

A preferred solid, in particular powdered, washing agent according to the invention can also contain, in addition to the compound according to the invention, in particular components that are selected e.g. from the following:
- anionic surfactants, such as preferably alkylbenzene sulfonate, alkyl sulfate, e.g. in quantities of preferably 5-30 wt. %
- nonionic surfactants, such as preferably fatty alcohol polyglycol ether, alkyl polyglucoside, fatty acid glucamide, e.g. in quantities of preferably 0.5-15 wt. %
- builders, such as e.g. zeolite, polycarboxylate, sodium citrate, in quantities of e.g. 0-70 wt. %, advantageously 5-60 wt. %, preferably 10-55 wt. %, in particular 15-40 wt. %,
- alkalis, such as e.g. sodium carbonate, in quantities of e.g. 0-35 wt. % advantageously 1-30 wt. %, preferably 2-25 wt. %, in particular 5-20 wt. %,
- bleaching agents, such as e.g. sodium perborate, sodium percarbonate, in quantities of e.g. 0-30 wt. % advantageously 5-25 wt. %, preferably 10-20 wt. %,
- corrosion inhibitors, e.g. sodium silicate, in quantities of e.g. 0-10 wt. %, advantageously 1-6 wt. %, preferably 2-5 wt. %, in particular 3-4 wt. %,
- stabilizers, e.g. phosphonate, advantageously 0-1 wt. %,
- foam inhibitor, e.g. soap, silicone oils, paraffins, advantageously 0-4 wt. %, preferably 0.1-3 wt. %, in particular 0.2-1 wt. %,
- enzymes, e.g. proteases, amylases, cellulases, lipases, advantageously 0-2 wt. %, preferably 0.2-1 wt. %, in particular 0.3-0.8 wt. %,
- anti-grays, e.g. carboxymethyl cellulose, advantageously 0-1 wt. %,
- discoloration inhibitor, e.g. polyvinylpyrrolidone derivatives, preferably 0-2 wt. %,
- adjusting agents, e.g. sodium sulfate, advantageously 0-20 wt. %,
- optical brighteners, e.g. stilbene derivatives, biphenyl derivatives, advantageously 0-0.4 wt. %, in particular 0.1-0.3 wt. %,
- optionally further scents
- optionally water
- optionally soap
- optionally bleach activators
- optionally cellulose derivatives
- optionally soil repellents, wt. % based in each case on the total agent.

In another preferred embodiment of the invention, the agent is present in liquid form, preferably in gel form. Preferred liquid washing or cleaning agents contain water as the main solvent and optionally non-aqueous solvents.

A preferred liquid, in particular gel, washing agent according to the invention can also contain, in addition to the compound according to the invention, in particular components that are selected e.g. from the following:
- anionic surfactants, such as preferably alkylbenzene sulfonate, alkyl sulfate, e.g. in quantities of preferably 5-40 wt. %
- nonionic surfactants, such as preferably fatty alcohol polyglycol ether, alkyl polyglucoside, fatty acid glucamide, e.g. in quantities of preferably 0.5-25 wt. %
- builders, such as e.g. polycarboxylate, sodium citrate, advantageously 0-15 wt. %, preferably 0.01-10 wt. %, in particular 0.1-5 wt. %,
- foam inhibitor, e.g. soap, silicone oils, paraffins, in quantities of e.g. 0-10 wt. %, advantageously 0.1-4 wt. %, preferably 0.2-2 wt. %, in particular 1-3 wt. %,
- enzymes, e.g. proteases, amylases, cellulases, lipases, in quantities of e.g. 0-3 wt. %, advantageously 0.1-2 wt. %, preferably 0.2-1 wt. %, in particular 0.3-0.8 wt. %,
- optical brighteners, e.g. stilbene derivative, biphenyl derivative, in quantities of e.g. 0-1 wt. %, advantageously 0.1-0.3 wt. %, in particular 0.1-0.4 wt. %,
- optionally further scents,
- optionally stabilizers,
- water,
- optionally soap, in quantities of e.g. 0-25 wt. %, advantageously 1-20 wt. %, preferably 2-15 wt. %, in particular 5-10 wt. %,
- optionally solvents (preferably alcohols), advantageously 0-25 wt. %, preferably 1-20 wt. %, in particular 2-15 wt. %, wt. % based in each case on the total agent.

A preferred liquid fabric softener according to the invention can also contain, in addition to the compound according to the invention, in particular components that are selected from the following:
- cationic surfactants, such as in particular esterquats, e.g. in quantities of 2-30 wt. %,
- co-surfactants, such as e.g. glycerol monostearate, stearic acid, fatty alcohols, fatty alcohol ethoxylates, e.g. in quantities of 0-5 wt. %, preferably 0.1-4 wt. %,
- emulsifiers, such as e.g. fatty amine ethoxylates, e.g. in quantities of 0-4 wt. %, preferably 0.1-3 wt. %,
- optionally further scents
- dyes, preferably in the ppm range stabilizers, preferably in the ppm range
solvents, such as e.g. water, in quantities of preferably 60-90 wt. %,
wt. % based in each case on the total agent.

The invention also provides a method for the long-lasting scenting of surfaces, wherein a compound according to one of formulae (I) and/or (III) to (XIV) or a washing or cleaning agent according to the invention is applied onto the surface to be scented (e.g. textile, dishes, floor) and the said surface is then exposed to an electromagnetic radiation comprising the wavelengths of 200 to 400 nm.

The invention also provides a method for long-lasting room scenting, wherein a room-scenting agent according to the invention is exposed to an electromagnetic radiation comprising the wavelengths of 200 to 400 nm.

EXAMPLES

Example 1

Production of the Pro-Fragrances According to the Invention

Step 1

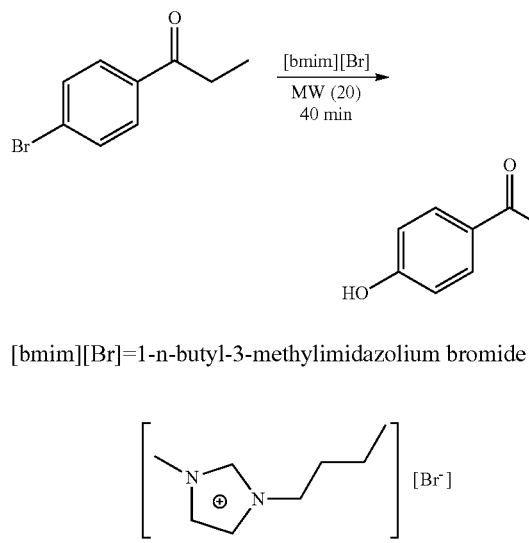

[bmim][Br]=1-n-butyl-3-methylimidazolium bromide

A microwave vial was initially charged with 0.35 ml (2 mmol) of methoxypropiophenone and 1.32 g (6 mmol) of [bmim][Br], flooded with protective gas and sealed with a septum. The sample was allowed to react in the microwave and under the following conditions:
maximum temperature=220° C.
maximum pressure=12 bar
maximum output=20 watts (varied)
time=40 min After cooling the sample, 0.1M HCl (pH=1) was added to the reaction mixture and extraction was performed 3 times with EtOAc. The combined organic phases were washed with saturated NaCl solution, dried over MgSO$_4$, filtered and the solvent was removed under vacuum. The desired product could be detected by GC/MS and $^1$H-NMR spectroscopy. The yield was 0.27 g (90%).

GC/MS: m/z: 150, 121, 93, 65, 53.
$t_R$=12.044 min
$^1$H-NMR: (400 MHz, CDCl$_3$, TMS)
δ (ppm)=7.91 (d, 2H); 6.90 (d, 2H); 5.29 (s, 1H); 2.95 (q, 2H), 1.22 (t, 3H).

Step 2

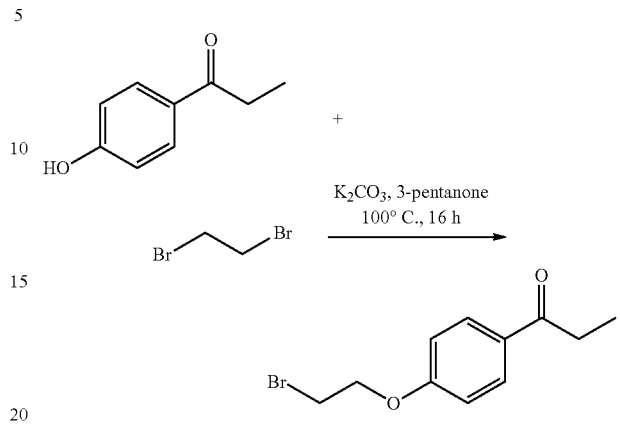

A round-bottomed flask was initially charged with 2 eq K$_2$CO$_3$ and 1 eq hydroxypropiophenone in 3-pentanone. To this was added 1 eq 1,2-dibromoethane and the mixture was stirred under reflux for 16 h. After cooling, the mixture was filtered, the solid was washed 2× with 3-pentanone and the combined phases were concentrated under reduced pressure.

Column chromatography was performed (1:3 EtOAc/pet. ether).

Step 3

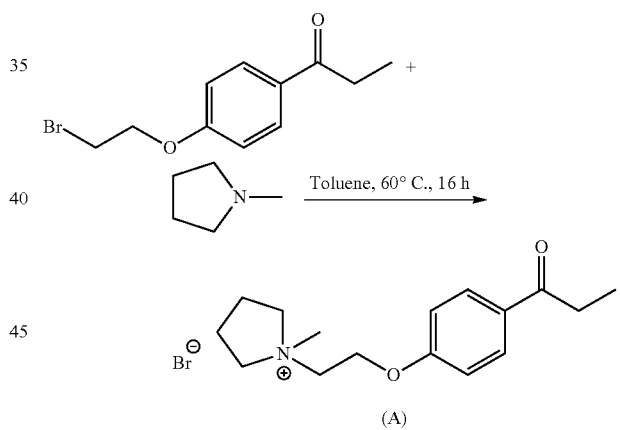

A round-bottomed flask was initially charged with the product obtained in step 2 and an excess of N-methylpyrrolidine in toluene, and the mixture was stirred at 60° C. for 16 h and worked up after cooling.

Other quaternary ammonium residues can be prepared in the same way as in step 3.

Step 4

Preparation of a compound of general formula (I) from compound (A) from step 3 and delta-damascene 8.50 g of diisopropylamine in 210 ml of THF were taken as the initial charge under nitrogen and the solution was cooled to −78° C. This was followed by the addition of 14.1 g of compound (A) from step 3 and then the addition of 40.3 ml of a butyllithium solution (2.5 molar in hexane; corresponding to 100.8 mmol). The reaction solution was stirred for 1 hour at −78° C. Then, with stirring, 24 g of dried cerium chloride were added (cerium III chloride, dried; corresponding to 98 mmol; produced from: cerium III chloride.7H$_2$O by drying for six hours at 150° C. in a high vacuum). The reaction solution was then stirred for 30 minutes at −78° C. Next, 14.8 g of delta-damascone were added slowly, dropwise, using a dropping funnel and stirring of the reaction solution continued at −78° C. The cooling was then removed and, at a temperature of approx. −10° C., the addition of a saturated ammonium chloride solution took place. For purification purposes, extraction was performed 3 times with 350 ml ether each time and the resulting light-yellow organic phase was then shaken out with water and later with saturated NaCl solution. The organic phase was then dried over magnesium sulfate. The filtrate was freed of solvent under reduced pressure. The resulting crude product was finally distilled in a high vacuum. The desired target product was obtained in a quantity of 29 g.

The reaction to form further compounds of general formula (I) with other scent ketones and with scent esters took place in the same way as for step 4.

The compound produced in this way displayed a very good scent effect when used in washing agents and fabric softeners in textile treatment. In particular, better persistence of the scent impression was found on the laundry that had been washed therewith and then dried, compared with washing agents and fabric softeners which contained an equivalent quantity of delta-damascone but were otherwise the same. The fresh scent impression of the textiles persisted for significantly longer, both after line drying and in particular after drying in an automatic dryer.

Example 2

Smell Test

The compounds to be compared were dissolved in 0.1 mmol in dichloromethane with 250 μl in each case applied onto cotton cloths measuring 5×5 cm. After evaporation of the solvent, they were immersed several times in a beaker with 500 ml of washing liquor (made from commercially available washing agent without perfume substances in a conventional domestic concentration) and finally rinsed with tap water. They were then irradiated freshly or after drying (in the dark) with UV light of 366 nm (t=5 min). The odor intensity was evaluated by a panel of 6 trained persons. The odor intensity was scored on a scale of 1 to 6, for which the following applies:
1=very weak
2=weakly perceptible
3=clearly perceptible
4=strongly perceptible
5=intense
6=very intense The samples were then stored in the dark. The irradiation and subsequent evaluation of intensity were repeated after the specified time intervals (1 day, 3, 7 and 14 days).

|  | fresh | 1 day | 3 days | 7 days | 14 days |
|---|---|---|---|---|---|
| Compound of formula (I) without quaternized ammonium group of formula (II) (comparative test) | 3 | 3 | 3 | 2 | 1 |
| Compound of formula (I) with quaternized ammonium group of formula (II) (according to the invention) | 4 | 4 | 4 | 3 | 3 |
| Scent without compound of formula (I) (comparative test) | 6 | 3 | 2 | 2 | 1 |

The tests and comparative tests that were performed clearly show that the compounds according to the invention of formula (I) with a quaternized ammonium group of formula (II) bring about a clear increase in fragrance intensity after just one day compared with a compound of formula (I) without a quaternized ammonium group of formula (II) or compared with the simple unmodified scent. The tests prove that the compounds according to the invention are particularly effective pro-fragrances and attach particularly well to surfaces.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A compound of the general formula (I),

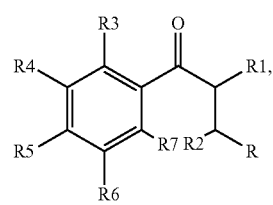

Formula (I)

wherein R denotes a substituted hydrocarbon residue with 2 to 20 C atoms, having at least one carbonyl group or ester group, R1, R2 each, independently of one another, denote hydrogen, a linear or branched, substituted or unsubstituted alkoxy group with 1 to 15 C atoms, a linear or branched, substituted or unsubstituted alkyl group or alkenyl group with 1 to 15 C atoms or a substituted or unsubstituted aryl residue, R3, R4, R5, R6 and R7 each, independently of one another, denote hydrogen, an amino group, —NO$_2$, a linear or branched, substituted or unsubstituted alkoxy group with 1 to 15 C atoms, a linear or branched, substituted or unsubstituted alkyl group with 1 to 15 C atoms, a cycloalkyl residue, acyl residue, aryl residue, —OH, —NH$_2$, halogen, NH-alkyl or —N(alkyl)$_2$, and wherein at least one of the residues R3, R4, R5, R6, R7 denotes a quaternary ammonium residue of formula (II),

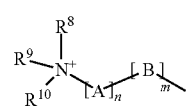

(II)

wherein
A denotes a CH$_2$ or a CH$_2$CH$_2$O group with n=1 to 20 and B denotes oxygen with m=0 or 1, wherein m=0 if A is a CH$_2$CH$_2$O group and R8, R9, R10 each, independently of one another, denote H or a substituted or unsubstituted, alkyl, cycloalkyl, alkenyl, aryl or acyl group-containing residue, and wherein two of the residues R8, R9, R10 can in each case be joined together by ring closure.

2. The compound according to claim 1, characterized in that the substituents R1 and R2, independently of one another, denote a linear or branched, substituted or unsubstituted alkyl group with 1 to 6 C atoms, preferably 1 to 3 C atoms, in particular in each case a methyl residue.

3. The compound according to claim 1, wherein substituents R3, R4, R6 and R7 each denote hydrogen, and wherein the residue R5 denotes a quaternary ammonium residue of formula (II),

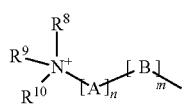
(II)

wherein

A denotes a CH$_2$ or a CH$_2$CH$_2$O group with n=1 to 20 and
B denotes oxygen with m=0 or 1, wherein m=0 if A is a CH$_2$CH$_2$O group and R8, R9, R10 each, independently of one another, denote H or a substituted or unsubstituted, alkyl, cycloalkyl, alkenyl, aryl or acyl group-containing residue, and wherein two of the residues R8, R9, R10 can in each case be joined together by ring closure.

4. The compound according to claim 1, wherein R denotes a substituted hydrocarbon residue with 2 to 20 C atoms, which has at least one ester group, and R2 denotes a substituted or unsubstituted aryl residue.

5. The compound according to claim 1, wherein R denotes a substituted hydrocarbon residue with 2 to 20 C atoms and R2 denotes a linear or branched, substituted or unsubstituted alkyl group or alkenyl group with 1 to 15 C atoms.

6. The compound according to claim 1, wherein R denotes a substituted hydrocarbon residue with 2 to 20 C atoms substituted with a cyclic alkenyl residue that has at least one carbonyl group and R2 denotes a linear or branched an alkyl group with 1, 2 or 3 C atoms.

7. The compound according to claim 1, corresponding to one of the following formulae (III) to (X)

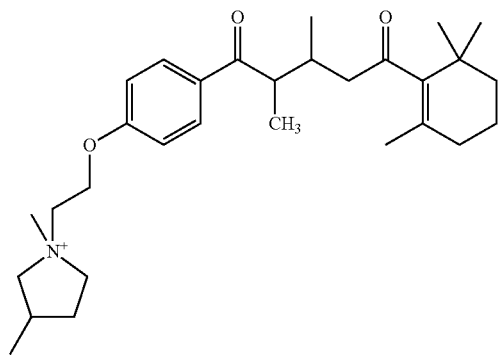
(III)

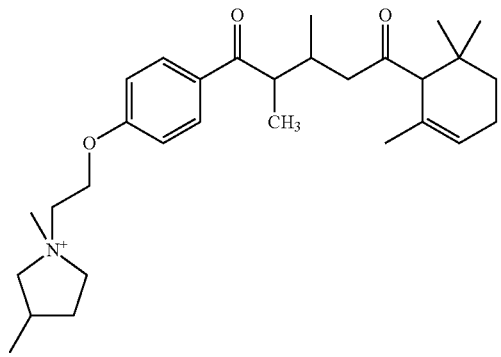
(IV)

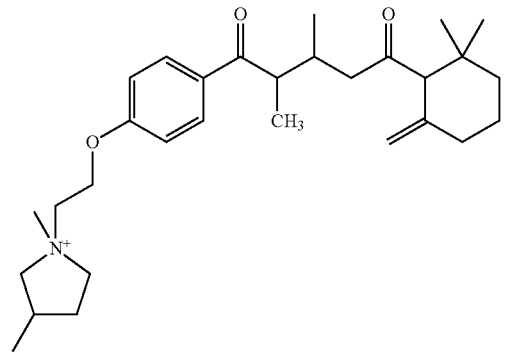
(V)

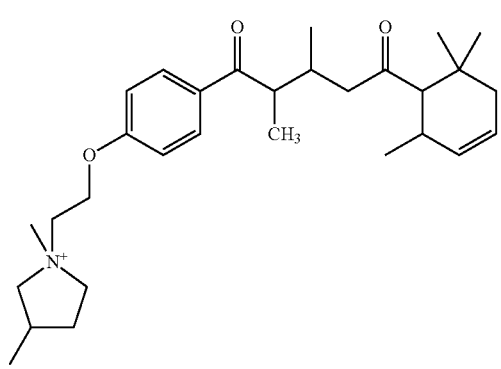
(VI)

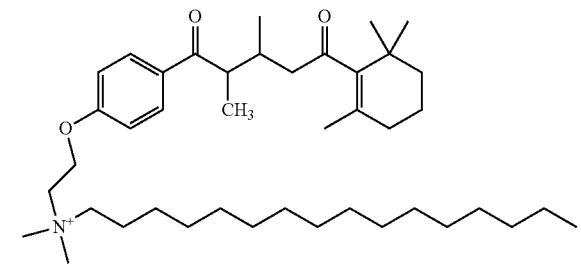
(VII)

(VIII)
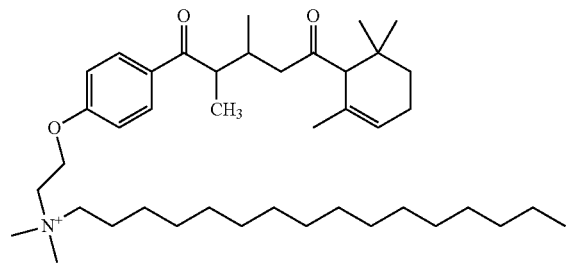
(IX)
(X)
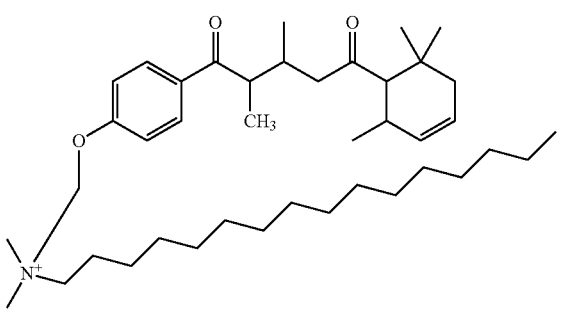
* * * * *